United States Patent [19]

Carduck et al.

[11] Patent Number: 5,185,457
[45] Date of Patent: Feb. 9, 1993

[54] PROCESS FOR THE CONTINUOUS PRODUCTION OF FATTY ACID SOAPS

[75] Inventors: Franz-Josef Carduck, Haan; Hubert Harth, Duesseldorf; Harald Liebs, Leverkusen, all of Fed. Rep. of Germany

[73] Assignee: Henkel Kommanditgesellschaft auf Aktien, Duesseldorf-Holthausen, Fed. Rep. of Germany

[21] Appl. No.: 237,796

[22] Filed: Aug. 29, 1988

[30] Foreign Application Priority Data

Aug. 28, 1987 [DE] Fed. Rep. of Germany ....... 3728811

[51] Int. Cl.$^5$ .................. C07F 5/00; C07C 51/10; C07C 51/00
[52] U.S. Cl. ........................ 554/71; 554/72; 554/76; 554/129; 554/132; 554/154
[58] Field of Search .......... 260/413, 414; 554/129, 554/132, 154, 71, 76, 72

[56] References Cited

U.S. PATENT DOCUMENTS

| | | | |
|---|---|---|---|
| 3,334,842 | 8/1967 | Pillar et al. | 242/177 |
| 3,531,495 | 9/1970 | Burton et al. | 260/309.2 |
| 3,787,160 | 1/1974 | Leister | 425/208 |
| 3,803,188 | 4/1974 | Scott et al. | 260/413 S |
| 4,294,771 | 10/1991 | Piertralla et al. | 260/413 S |

FOREIGN PATENT DOCUMENTS

| | | |
|---|---|---|
| 163395 | 4/1985 | European Pat. Off. |
| 58-164540 | 9/1983 | Japan ................. 260/414 |
| 174615 | 11/1965 | U.S.S.R. ............. 260/414 |
| 989330 | 1/1964 | United Kingdom . |
| 1074093 | 6/1967 | United Kingdom . |
| 2103616 | 2/1982 | United Kingdom . |

Primary Examiner—Jose G. Dees
Assistant Examiner—Joseph M. Conrad
Attorney, Agent, or Firm—Ernest G. Szoke; Wayne C. Jaeschke; Daniel S. Ortiz

[57] ABSTRACT

A process for the continuous production of fatty acid soaps by reaction with solid metal oxides, hydroxides, hydrogen carbonates and carbonates of Mg, Ca, Ba, Pb, Al, Zn, Co, Fe, Cd and Zr, in which the fatty acids are subjected to a rotational movement by mechanical transport and the metal compounds are subjected to rotation in the opposite direction by mechanical transport, the two reactants are combined in the reaction zone of a tube reactor and are reacted in 0.5 to 50 seconds.

3 Claims, No Drawings

PROCESS FOR THE CONTINUOUS PRODUCTION OF FATTY ACID SOAPS

BACKGROUND OF THE INVENTION

1. Field of the Invention

This invention relates to a process for the continuous production of fatty acid soaps by reaction of fatty acids with solid metal compounds selected from the series of oxides, hydroxides, hydrogen carbonates and carbonates of metals from the group formed by alkaline earth metals, such as magnesium, calcium and barium, and by lead, aluminum, zinc, cobalt, iron, cadmium and zirconium, optionally in the presence of up to 10% by weight water, based on the total weight of the reactants.

2. Statement of Related Art

The fatty acid soaps to be produced in accordance with the invention are understood to be compounds which are formed by neutralization of fatty acids with stoichiometric quantities of metal oxides, hydroxides, hydrogen carbonates and carbonates or with an excess of these basic metal compounds. Metal soaps are used for many purposes. Calcium soaps, particularly basic calcium soaps, for example soybean oil fatty acid and palm oil fatty acid calcium soaps, are used for the feeding of ruminants; dibasic lead stearate and complex metal/calcium stearates are known additives for the processing of PVC.

Metal soaps can be produced in batches by reaction of a molten fatty acid with a suspension or solution of metal oxides or hydroxides and then filtering and drying the soaps formed. However, this process is complex because the reaction mixture must be diluted sufficiently to remain stirrable. In addition, considerable energy is consumed in drying the soap to a free-flowing product.

Some basic soaps, for example basic lead stearates, can be produced molten in batches, by introducing the metal oxide or hydroxide into a stirred melt of the fatty acid. In processes such as these, product discoloration can occur as a result of the prolonged heating involved. The basic soaps of alkaline earth metals cannnot be produced by this process since they are infusible materials.

Other basic soaps, for example the calcium soap of palm oil fatty acid, can be produced in batches in a so-called heating mixer (fluid mixer), of the type normally used in the processing of PVC, by introducing the metal oxide or hydroxide into the molten fatty acid. The temperature of the reaction mixture rises and the water of reaction partially evaporates under the effect of the heat of neutralization and the energy introduced by the mixer. After the starting materials have fully reacted, the reaction mixture changes from a viscous material to a solid. This solid material may be cooled and size-reduced. During the change from the viscous phase to the solid phase, however, the mixer begins to vibrate to an extent which cannot be controlled in a reactor of a few 100 liters capacity which is required for commercial production. In addition, the fluid mixers mentioned above are known for their high consumption of electricity. Accordingly, the process in question is only suitable for the production of small quantities in laboratories and pilot plants.

EP-A 0 163 395 describes a process for the production of metal soaps, in which a pumpable mixture is prepared from molten fatty acids and basic metal compounds, such as calcium oxide, and is spread out over a conveyor belt to complete the reaction and to remove the water formed during the reaction. The reaction product obtained has to be size-reduced which poses technological problems in view of the large quantities to be handled and the solid consistency of the fully reacted fatty acid soaps.

BRIEF DESCRIPTION OF THE INVENTION

Other than in the operating examples, or where otherwise indicated, all numbers expressing quantities of ingredients or reaction conditions used herein are to be understood as modified in all instances by the term "about".

Accordingly, there is a need for simple, inexpensive and product-protecting processes for the production of metal soaps. It has now surprisingly been found that the metal soaps can be produced by a) subjecting molten at least one fatty acid, heated to a temperature of 20 to 150° C., to a rotation in a first direction by mechanical transport and transporting the fatty acid into a reaction zone of a tube reactor, b) subjecting the at least one metal compound to a rotation movement by mechanical transport, in a second direction opposite to the first direction of rotation of the fatty acid and transporting the metal compound into the reaction zone in the vicinity of the an axis of rotation of the fatty acid in the reaction zone to form a mixture, c) reacting the mixture of fatty acid and metal compound in the reaction zone of the tube reactor for about 0.5 to about 50 seconds, the mixture being mechanically transported with rotation in the direction of rotation of the fatty acid through the reaction zone and d) recovering the fatty acid soap at the exit from the reaction zone.

The reaction product leaving the tube reactor is thinly liquid to viscous and solidifies on cooling. In the case of basic calcium soaps, the reaction product is obtained in the form of flakes which can be readily size-reduced to powder. By virtue of the fact that the reaction product leaves the tube reactor after it has completely or almost completely reacted, the formation of compact materials difficult to size-reduce can be prevented.

DETAILED DESCRIPTION OF THE INVENTION

The reaction velocity and the consistency of the reaction product can be adjusted by variation of the mixing intensity in the tube reactor, the reactor temperature and the quantity of fatty acids introduced. Fatty acids having an acid value of 180 to 200 mg KOH/g give soaps having a residual acid value of around 1 mg KOH/g.

Metal oxides, metal hydroxides, mixtures of oxides and hydroxides of the same or different metals and also hydrogen carbonates and carbonates, optionally in admixture with oxides and hydroxides, are used as the basic components. The basic components are present preferably in a quantity of 1 to 3 equivalents of the metal compounds per mole fatty acid. It is possible to use both pure fatty acid and also fatty acid mixtures, for example soybean oil fatty acid, palm oil fatty acid or stearin. Impurities in the form of triglycerides and unsaponifiable materials do not adversely affect the process. In some cases, particularly where metal oxides and carbonates are used, it can be of advantage to introduce small quantities of water into the mixer to start the reaction. Since water is inevitably formed during the reaction, the upper limit to the quantity of water added is 10% by weight.

The process according to the invention also provides for the introduction of additives which do not take part in the neutralization process. Thus, in the production of basic calcium soaps for the feeding of ruminants, it is possible to add other feeds, for example soybean meal, so that the soybean meal is coated with the calcium soaps. In the production of basic lead stearate, it is possible for example to add various liquid esters such as described in EP-A 0 184 128 and 0 184 129, so that ready-to-use compositions for the extrusion of PVC are formed.

Continuous mixers which develop high mixing and shearing intensity in a small space through high-speed, spiral, preferably according to the invention. Continuous mixers such as these provide for the complete reaction of the solid basic component with the liquid fatty acids. Through the brief residence time in the mixer, the reaction mixture can solidify outside the mixer and the reaction products are not overheated.

A reactor suitable for carrying out the process according to the invention comprises a tube reactor provided with high-speed feed elements comprising a) a feed zone and a reaction zone arranged one behind the other along the tube axis,
b) an outer tube closed at one end which forms the outer boundary of the feed zone and reaction zone,
c) an inner tube extending coaxially from the closed end of the outer tube over the length of the feed zone into the outer tube,
d) an outer, coaxially rotating screw element arranged in the annular space—forming the feed zone—between the outer tube and the inner tube and in the reaction zone and
e) an inner, coaxially rotating screw element which is arranged in the inner tube and which rotates in the opposite direction to the outer screw element.

In one preferred embodiment of the invention, the reaction zone end of the inner screw element projects from the inner tube surrounding the screw element by a distance corresponding to approximately one screw thread.

The process of the invention can be carried out in a continuous injection mixer (for example as described and illustrated in a publication entitled FMC 058 Kontinuierlicher Einspritzmischer) or a similar device. In practice, the fatty acid is fed in the molten state into the annular space forming the feed zone between the outer tube and the inner tube and is fed into the reaction zone by means of spiral elements. The solid metal compounds are fed through the inner tube by means of a rotating spiral which rotates in the opposite direction to the outer spiral. The required homogeneous reaction mixture is formed when the components rotating in opposite directions meet one another.

The water of reaction formed partially evaporates as the reaction product leaves the mixer. For certain applications, for example for basic calcium soaps for the feeding of ruminants, the water of reaction may remain in the product. In cases such as these, the reaction mixture may be spread over a cooling belt or cooling rollers and solidified by cooling. The solid basic soaps may then be reduced to the required particle size. However, the reaction mixture may also be solidified by spraying into a stream of cold air or may be sprayed onto a fluidized bed of already solidified basic soap. If the presence of water of reaction in the product cannot be tolerated, as for example in the processing of PVC, it has to be removed from the reaction mixture. This may be done, for example, by introducing the reaction mixture into a continuous kneader fitted with a discharge screw. The water is removed from this kneader in vacuo in the vapor phase. By cooling the discharge screw, a product is obtained which may be extruded through perforated discs to form strands which, after cooling, may be reduced to a cylindrical granulate.

Instead of using a kneader, it is also possible to use continuous hollow screws, heat exchangers, vented extruders and related machines.

As can be seen from the foregoing description, the process according to the invention is distinguished by low investment costs, minimal energy consumption and particular simplicity.

The process according to the invention is illustrated by the following Example.

EXAMPLE

A tube reactor of the type described above having the following specification was used:
reactor length (sum of feed zone and reaction zone): 840 mm;
overall length of the inner tube: 950 mm, including an approx. 200 mm inside the outer tube;
internal diameter of the outer tube: 84 mm;
internal diameter of the inner tube: 40 mm;
external diameter of the outer mixing spiral: 75 mm;
internal diameter of the outer mixing spiral: 55 mm;
rotational speed of the outer and inner mixing spirals: 900 min$^{-1}$.

The jacket of the tube reactor was filled with water at 60° C. The inner tube of the reactor was continuously charged with 91 kg/h Ca(OH)$_2$. 413 kg/h soybean oil fatty acid (acid value 186 mg KOH/g) at 56° C. were continuously introduced into the outer mixing tube. These conditions correspond to a residence time of the reactants in the reaction zone of 1-5 seconds.

The viscous reaction product issuing from the mixer had a residual acid value of 1.0 mg KOH/g and an exit temperature of 65° C. It was continuously distributed over a water-cooled steel belt (width 600 mm, length 10 m) and cooled. Flakes were obtained and were reduced to powder using a so-called rasp (of the R300 type made by Alexander-Werke). The resulting basic calcium soap of soybean oil fatty acid having a calcium content of 9.5% by weight was eminently suitable as a feed additive for ruminants.

We claim:
1. A process for the continuous production of fatty acid soap by reaction of at least one fatty acid with at least one metal oxide, metal hydroxide, metal hydrogen carbonate, or metal carbonate of metals selected from the group consisting of alkaline earth metals, lead, aluminum, zinc, cobalt, iron, cadmium and zirconium which comprises:
a) introducing a molten fatty acid, heated to a temperature of about 20 to about 150° C., having a rotational movement in a first direction about an axis of rotation in a reaction zone,
b) introducing the metal compound having a rotational movement in a second direction, opposite to the first direction of rotation of the fatty acid, into the reaction zone in the vicinity of the axis of rotation of the fatty acid to form a mixture, c) reacting the mixture of fatty acid and metal compound in the reaction zone for about 0.5 to about 50 seconds, the mixture being, passed through the reaction zone with rotation in the direction of rotation of the fatty acid, and d) recovering fatty acid soap from the reaction zone.

2. A process as claimed in claim 1, wherein 1 to 3 equivalents of the metal compounds per mol fatty acid are introduced into the reaction zone.

3. A process of claim 1 wherein the soap has an acid value of about 1 mg KOH/gram.

* * * * *